United States Patent [19]

Chaslow et al.

[11] Patent Number: 5,028,438
[45] Date of Patent: Jul. 2, 1991

[54] BIOLOGICALLY ACTIVE AGENT HAVING ANTI-HYPERTENSIVE ACTIVITY IN MAMMALS

[75] Inventors: Fred I. Chaslow, Glen Cove; H. Leon Bradlow, Holliswood, both of N.Y.

[73] Assignee: Long Island Jewish Medical Center, New Hyde Park, N.Y.

[21] Appl. No.: 130,805

[22] Filed: Dec. 9, 1987

Related U.S. Application Data

[63] Continuation-in-part of Ser. No. 939,552, Dec. 9, 1986.

[51] Int. Cl.$^5$ .......................... A61K 35/12; C07H 1/08
[52] U.S. Cl. ........................................ 424/537; 536/5; 536/127; 514/26; 514/807
[58] Field of Search ...................... 536/5, 127; 424/95, 424/537; 514/26, 807, 821, 870, 874

[56] References Cited

U.S. PATENT DOCUMENTS

| | | | |
|---|---|---|---|
| 3,329,567 | 7/1967 | Ruskin | 514/26 |
| 3,458,628 | 7/1969 | Kaiser et al. | 514/26 |
| 3,856,944 | 12/1974 | Satoh | 514/26 |
| 4,440,863 | 4/1984 | Haagensen, Jr. | 436/543 |
| 4,703,003 | 10/1987 | Struck | 435/68 |
| 4,780,314 | 10/1988 | Graves | 424/95 |

FOREIGN PATENT DOCUMENTS

| | | | |
|---|---|---|---|
| 0407348 | 5/1968 | Australia | 424/95 |
| 2707264 | 8/1978 | Fed. Rep. of Germany | 514/26 |
| 53-133617 | 11/1978 | Japan | 424/95 |
| 60-28987 | 2/1985 | Japan | 514/26 |
| 0741882 | 7/1980 | U.S.S.R. | 424/95 |
| 1186624 | 4/1970 | United Kingdom | 514/26 |

OTHER PUBLICATIONS

Goodman and Gilman's *The Pharmacological Basis of Therapeutics*, pp. 730, 753, 936–937, 6th Ed., 1980.
Raju et al., J. Endocrinol. Metab. 45(3):429–434 (1977).
Raju et al., J. Steroid Biochem. 20(48):1061–1065 (1984).
Raju et al., J. Clin. Endocrinol. Metab. 60(5):940–946 (1985).
Raju et al. Steroids 45(3–4);341–346 (1985).

*Primary Examiner*—Ronald W. Griffin
*Assistant Examiner*—Nancy S. Carson
*Attorney, Agent, or Firm*—Darby & Darby

[57] ABSTRACT

A biologically active agent extracted from female breast cyst fluids displays anti-hypertensive activity in mammals. The agent is also useful in the treatment of congestive heart disease, atrial fibrillation and idiopathic edema in mammals.

6 Claims, 8 Drawing Sheets

BIOLOGICALLY ACTIVE AGENT HAVING ANTI-HYPERTENSIVE ACTIVITY IN MAMMALS

FIELD OF THE INVENTION

This application is a continuation-in-part of U.S. patent application Ser. No. 939,552, filed Dec. 9, 1986 of Fred I. Chasalow and H. Leon Bradlow.

The present invention is directed to a novel biologically active agent isolated from human female breast cyst fluid. The new agent is useful in treating hypertension in mammals and can also be used to treat atrial fibrillation, idiopathic edema and congestive heart failure in mammals.

BACKGROUND OF THE INVENTION

The present invention is directed to a novel biologically active agent useful for the treatment of hypertension, congestive heart failure, atrial fibrillation and idiopathic edema in mammals.

Congestive heart disease is characterized by an incomplete emptying of blood from the heart during ventricular contraction, which leads to an enlargement of the heart. When treated with drugs (cardiac glycosides), there is a reduction of heart rate, a more complete filling of the ventricles, and the size of the heart decreases and begins to return to normal.

Atrial fibrillation is a condition in which the atria contract much more often than the ventricles, causing the lower heart chambers to be bombarded by impulses. The ventricles respond by weakly and inefficiently contracting. The drugs (cardiac glycosides) used to treat atrial fibrillation depress this conduction, slow the rate of the ventricular contraction and help re-establish a synchronous and effective heartbeat.

Digitalis, digoxin, ouabain and related steroid glycosides are a class of compounds known as cardiotoxic agents which enhance the force of contraction of the heart. One class of cardiotoxic agents, the cardiac glycosides (such as digitalis, digoxin and ouabain) are characterized by a basic cyclopentanoperhydrophenanthrene nucleus to which is attached an unsaturated lactone ring at C17. This structure, termed an aglycone, is combined with one to four molecules of sugar. The pharmacological action resides in the aglycone, but the sugar moieties affect solubilization properties and the potency of the resulting glycoside.

The most important therapeutic uses of cardiac glycoside drugs is in the treatment of congestive heart failure and atrial fibrillation. When digitalis is used to treat congestive heart failure, the beneficial effects produced have been attributed to the drug's positive inotropic (influencing muscular contractility) effect. The greater force of contraction resulting from administration of the drug increases the release of blood from the heart, increasing cardiac, output and improving systemic circulation.

One of the drawbacks of digoxin and its congeners is their low therapeutic index. There is a narrow window of concentrations in which the drugs are effective for the treatment of congestive heart failure or atrial fibrillation. In addition, there are numerous adverse side effects resulting from therapy with digoxin and related cardiac glycosides. These have been extensively reviewed by T.W. Smith et al. in *Prog. Cardiovas. Dis.* 26:21–56, 1984. Side effects of digoxin therapy include impotence, weakness, and depression. A further drawback is that some patients do not respond to digoxin treatment. Furthermore, digoxin and digitalis are only effective to depress blood pressure in patients that have previously suffered congestive heart failure and are ineffective in normal hypertensive patients. Ouabain is very rapid—acting has a half-life of 21 hours and is rapidly excreted by the kidneys. As a result, its use is limited to emergency treatment.

Hypertension is a common condition and is characterized by elevations of atrial pressure which could result in secondary organ damage and a reduced life-span. The condition is currently treated using four general classes of drugs: diuretics, anti-adrenergic agents, vasodilators and angiotension blockers (*Harrison's Principles of Internal Medicine*, K.J. Issel Bacher et al. eds, pp. 1172–1176, McGraw-Hill, New York 1980). Each of the above produce side effects and their use is limited. Cardiac glycosides (used to treat congestive heart disease) are essentially ineffective in treating hypertension.

Idiopathic edema is characterized by periodic episodes of edema or water retention. The current treatments available are non-specific and include administration of diuretics, beta adrenergic blockers such as propranolol, bed rest, and reduction in dietary salt intake.

A new active biological agent has now been unexpectedly derived from human breast cyst fluid. In particular, Type 1 human female breast cyst fluid has been found to contain a biologically active agent which can be administered to mammals to lower their blood pressure. The new biological agent crossreacts with specific antibodies to digoxin, a well known cardiac glycoside. Surprisingly, it was also found that the new biologically active agent stimulated the activity of the $Na^+K^+$-ATPase enzyme, unlike digoxin and related cardiac glycosides. The action of this enzyme provides a diuretic effect which may account for the observed hypotensive effect.

A principal object of the present invention is to provide a new biologically active agent.

A further object of the present invention is to provide a new biologically active agent, derived from human female breast cyst fluid, that has the property of lowering mammalian blood pressure and which can also be used to treat congestive heart failure, atrial fibrillation and idiopathic edema in mammals.

Another object of the present invention is to provide a method of treating hypertension in a mammal by administration of a biologically active agent derived from human female breast cyst fluid.

A still further object of the present invention is to provide a novel pharmaceutical formulation for treating hypertension in mammals comprising a biologically active agent derived from human female breast cyst fluid and pharmaceutically acceptable salts and/or carriers.

These and other objects of the present invention will be apparent to one of ordinary skill in the art in light of the present description, accompanying claims and appended drawings.

SUMMARY OF THE INVENTION

The present invention involves a biologically active agent isolated from human female breast cyst fluid. The new agent is immunoreactive with certain antibodies to digoxin, displays anti-hypertensive activity when administered to mammals, and can also be used to treat congestive heart failure, atrial fibrillation and idiopathic edema in mammals.

The present invention also provides a method for treating hypertension, congestive heart failure, atrial fibrillation or idiopathic edema in a mammal by administering an effective amount of the active biological agent isolated from human female breast cyst fluid to such a mammal.

The present invention also provides a method for purifying an active biological factor isolated from Type 1 human female breast cyst fluid. The purification method comprises mixing the raw female breast cyst fluid with a lower alcohol, followed by repeated extractions with solvents of decreasing polarity. The extracted factor is then subjected to sequential column chromatography.

DETAILED DESCRIPTION OF THE INVENTION

The novel biologically active agent of the present invention is isolated from human female breast cyst fluid.

It has recently been shown that fluid derived from cysts in the breasts of female humans with gross cystic disease contains a wide spectrum of biological molecules. Human female breast cyst fluid can be divided into two types, based on electrolyte composition. Type 1 fluid is characterized by having high levels of potassium and low levels of both sodium and chloride ions, whereas Type 2 fluid is characterized by having low levels of potassium and high levels of both sodium and chloride ions.

To obtain the biologically active agent of the invention, cyst fluid is isolated by needle aspiration from human females with gross cystic disease of the breast. The isolated fluid is frozen at $-20°$ C. until analyzed for its ionic composition. The fluid is then thawed and the ionic composition (i.e. concentration of sodium, chloride and potassium) determined by ion selective electrodes, using standard techniques that are well known in the art. Type 1 fluids, defined as having potassium and chloride concentrations greater than 100 meg/L and sodium concentrations less than 50 meq/L, are pooled and stored at $-20°$ C. until use.

After isolation and determination of ionic composition, the biologically active agent of the present invention is purified using organic solvents. Breast cyst fluid is first fractionated by the addition of a lower alcohol, preferably methanol, although ethanol, isopropanol or t-butanol can also be used. The alcohol supernatant containing the biologically active agent is further fractionated by the sequential addition of organic solvents of decreasing polarity. A preferred sequence of solvents is acetonitrile and acetonitrile:ethyl acetate (1:1). A wide variety of ion polarity organic solvents may be used in the extraction process. Thus, methyl acetate, propyl acetate, toluene, and benzene are non-limiting examples of the solvents that can be used as extraction agents. The biologically active agent can be stored for use at this point or, preferably, further purified by chromatography using a pressure stabilized polydextran, such as Sephasorb HP (Pharmacia, Piscataway, NJ) and additionally on Sephadex LH-20 (Pharmacia, Piscataway, NJ) using methanol as the eluant.

A particularly preferred purification regimen is conducted by agitating Type 1 human female breast cyst fluid with methanol, thereby causing precipitation of undesirable constituents in the fluid, and discarding the precipitate. The supernatant is then treated with acetonitrile. This causes precipitation of additional undesirable constituents. After discarding the precipitate, the methanol and acetonitrile are evaporated using a conventional rotary evaporator and a first aqueous phase containing the agent of the present invention is recovered. The first aqueous phase is further extracted with a solution of 1:1 acetonitrile/ethyl acetate, and an organic phase containing the active agent is obtained. The acetonitrile and ethyl acetate are removed from the organic phase and a second aqueous phase containing the agent is obtained. The second aqueous phase is then lyophilized and the lyophilizate extracted with methanol-water (1:1). The extract is then subjected to chromatography on a pressure stabilized polydextran column and fractions containing the biologically active agent are recovered. The fractions containing the active agent are identified by assaying for immunoreactivity with antibodies to digoxin as described below. The biologically active agent of the invention has been found to be immunoreactive with such antibodies. The methanol-water is then removed from the fractions containing the agent.

The active agent of the invention can be administered at this point or, preferably, first further purified by chromatography using a Sephadex LH-20 column. A particularly preferred regimen would comprise alternative sequential chromatography wherein Sephasorb HP and Sephadex LH-20 columns are employed. The sequence would be Sephasorb HP, Sephadex LH-20 using acetonitrile:water (7:3) as the eluant, Sephasorb HP and Sephadex LH-20 using methanol as the eluant.

Alternatively, the biologically active agent of the present invention can be extracted and purified from type I human female breast cyst fluids using the following more convenient procedure. After determination of its ionic composition, type I human breast cyst fluid is directly fractionated by two sequential additions of organic solvents of decreasing ionic polarity, as described above. However, this procedure eliminates the use of the lower alcohol extraction step described above. The thus fractionated agent is then subjected to sequential chromatography using hydrophobic affinity chromatography (e.g., Sephadex LH-20) and then an amino carbohydrate column. This streamlined extraction and purification procedure is illustrated in Example 5 below.

The advantages of using the above-described fractionation and chromatographic purification procedures are as follows: convenience, speed (the entire purification can be accomplished in 1 to 2 days) simplicity (only 2 column steps instead of 3 or 4) and increased purity of the final product. The latter is evidenced by the fact that in FIG. 8, only one peak of material absorbing light at 210 nm was detected when the fraction was subjected to chromatographic reanalysis. The ability to absorb light at 210 nm constitutes another characteristic of the active agent of the present invention in addition to the ability to bind to digoxin antibodies as explained below.

The active agent of the present invention may be detected by virtue of its ability to cross-react with antibodies to digoxin. Such antibodies are commercially available from New England Nuclear, Boston, MA (cat. no. A082). Alternatively, antibodies to digoxin obtained from Clinical Assays, Cambridge, MA (cat. no. 527) can also be used to assay for the presence of the biologically active agent of the present invention.

The assay for the active biological agent of the invention is carried out by adding a measured amount of the antibody and radioactively-labeled digoxin to an unknown solution. After allowing sufficient time for the antibody to bind, the bound and unbound material are separated by centrifugation. The presence of the agent in an unknown solution is detected in the bound fraction using a scintillation counter. The amount of the biologically active agent of the present invention is expressed as ng digoxin equivalents. 1 ng digoxin equivalent represents that amount of the biologically active agent required in this assay to produce a response obtainable with 1 ng of standard digoxin. A detailed description of this assay is presented below in Example 2.

The biologically active agent of the present invention displays properties (such as chromatographic behavior and digestion products) which suggest that it is a steroid conjugate.

The biologically active agent derived from Type 1 breast cyst fluids has been administered to mammals and has displayed a dramatic effect on lowering their blood pressure. Reductions in the blood pressure of healthy mammals of up to about forty-five percent (45%) as compared to initial (preadministration) blood pressure levels have been obtained upon administration of the active biological agent of this invention.

The purified biologically active agent of the present invention displays unique and unexpected properties. The agent stimulates the $Na^+K^+$-ATPase enzyme, whereas the cardiac glycosides digoxin and digitalis inhibit this enzyme activity. The $Na^+K^+$-ATPase enzyme has a mild diuretic action which may be of significance to the patient in terms of hypotensive activity. Therefore, the active agent isolated from Type 1 human female breast cyst fluid may be administered to mammals for treatment of conditions where sodium balance is upset, such as idiopathic edema.

In addition, the biologically active agent of the present invention was found to stimulate the binding of ouabain to its cellular receptor (shown below in Example 6). This is a most unexpected effect of the biologically active agent on the $Na+$, $K+$-ATPase system. Since the biologically active agent of the present invention stimulates the activity of the $Na+$, $K+$-ATPase, it was expected that it would inhibit the binding of ouabain to its receptor. Unexpectedly, however, the biologically active agent of the present invention increases the amount of ouabain that binds to its receptor. The present inventors are unaware of any other substance displaying this property.

The agent isolated from Type 1 human female breast cyst fluid is an endogenous hypotensive factor. Due to these properties, it is anticipated that this type of substance will be useful not only in treatment of diseases where digitalis or digoxin or ouabain are now currently employed, but also as a general anti-hypertensive agent. In addition, it is anticipated that the agent of the present invention, used in combination with ouabain, will increase the effectiveness of ouabain and therefore its use.

For treating mammals afflicted with elevated blood pressure using the biologically active agent, the effective dosage of the compounds of this invention depends upon the severity of conditions, the stage and the individual characteristics of each mammal being treated. For treating hypertension, congestive heart failure or atrial fibrillation in a mammal, it is expected that the compositions will generally be administered in a dosage range from about 10 ng digoxin equivalents to about 1000 ng digoxin equivalents per kg of body weight per day. Similar dosages and regimens would be employed for treatment of idiopathic edema and other diseases characterized by sodium imbalance.

The novel agent of the present invention may be administered via the parenteral route (which is preferred), but can also be administered orally, intranasally or by transdermal patch in pharmaceutical compositions prepared by well-known methods. Examples of parenteral dosage forms include aqueous solutions of the active agent in isotonic saline, 5% glucose or other well known pharmaceutically acceptable liquids. The pharmaceutical compositions can be formulated so as to be suitable for oral administration. The active ingredient is contained in a capsule (in liquid form) or tablet. The quantity of effective dose supplied by each capsule or tablet is relatively unimportant since the total dosage can be reached by administration of either one or a plurality of capsules or tablets or both. The capsules employed may comprise any well known pharmaceutically acceptable material such as gelatin, cellulose derivatives, etc. Each capsule contains an appropriate amount of the biologically active agent dissolved in a suitable solvent comprising, e.g. polyethylene glycol USP, ethylene glycol USP, ethyl alcohol USP, purified water USP and mixtures thereof. The tablets may be formulated in accordance with conventional procedure employing solid carriers, lubricants, etc., well known in the art. Examples of solid carriers are: starch, sugar, bentonite and other commonly used carriers. The biological agent of the present invention can also be dried and administered in the form of a hard shell tablet or a capsule containing, for instance, lactose or mannitol as a binder and conventional fillers and tabletting agents.

The invention is further illustrated in the specific examples set forth below which are intended to describe the invention without limiting its scope. Methods for the extraction, purification, characterization and utilization of the endogenous biologically active agent are presented in these examples.

EXAMPLE 1

Isolation of the Biologically Active Agent From Human Female Breast Cyst Fluid

Step 1: Extraction 250 ml of methanol was added to 250 ml of Type 1 human female breast cyst fluid, obtained by needle biopsy from women with gross cystic disease of the breast. The mixture was centrifuged at 16,000×g to remove denatured proteins and other insoluble material. The precipitate was discarded. The residual supernatant was mixed with an equal volume (500 ml) of acetonitrile, allowed to stand for ten minutes at room temperature and centrifuged to remove denatured and insoluble materials. The precipitate was discarded. The acetonitrile and methanol were removed under vacuum in a rotary evaporator (Buchler, Fort Lee, NJ) with a water bath at 40° C. The aqueous phase (200 ml) was re-extracted with a mixture of 200 ml acetonitrile and 200 ml of ethyl acetate. The lower aqueous layer was discarded and the organic phase removed under vacuum as above. The water (63 ml) remaining was removed from the extract by lyophilization. The solid material was extracted with 10 ml of methanol-water (1:1) and any insoluble material was eliminated by centrifugation as above.

The final extract was placed in serum vials and the methanol-water solvents removed under a stream of nitrogen gas at room temperature. The final product (K3) contained 1,800 ng digoxin equivalents of the biologically active agent which was equivalent to 7.2 ng digoxin equivalents in the original pooled sample.

Step 2: Chromatography on Sephasorb HP

Figure 1:
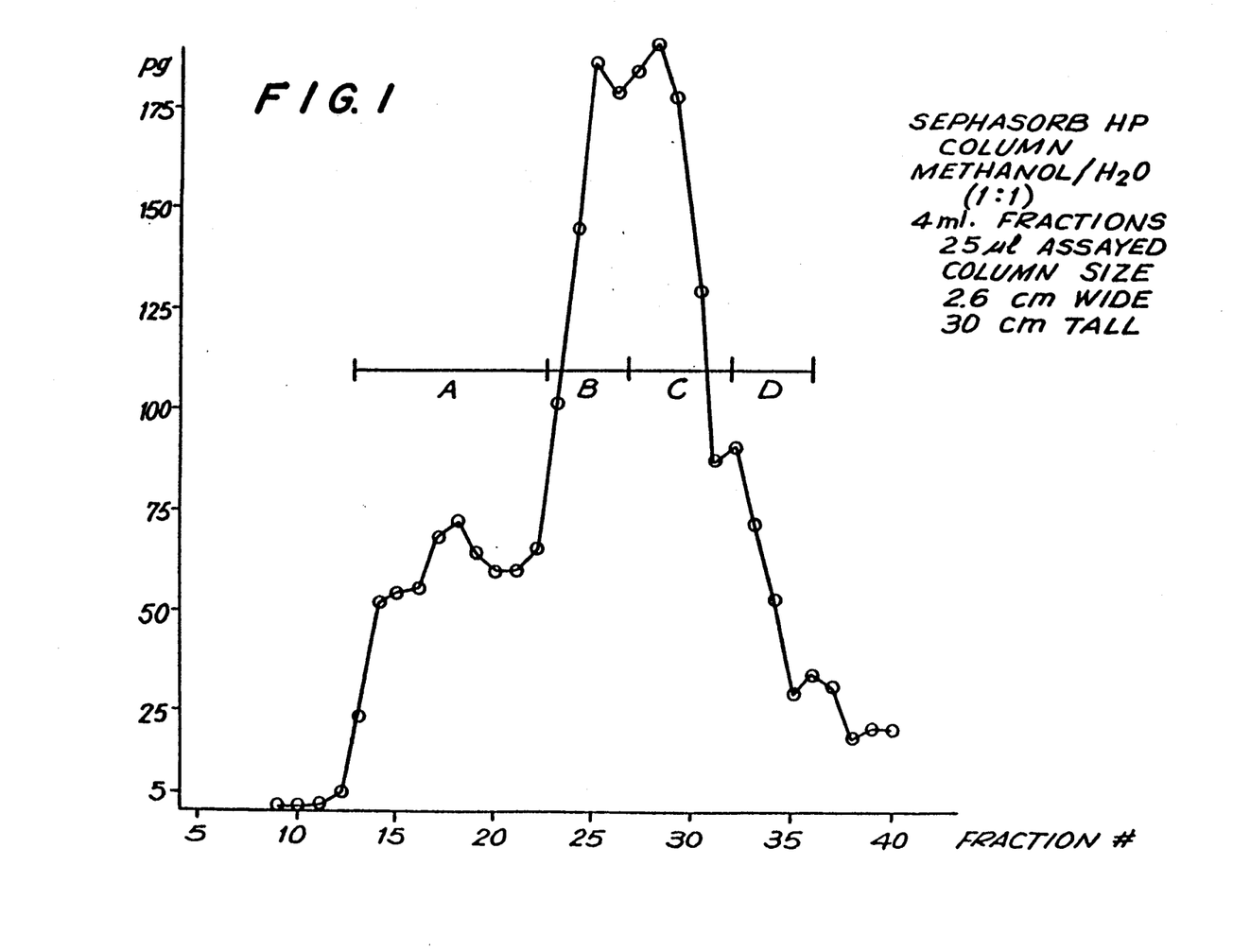
FIG. 1 is a plot of the elution profile from a Sephasorb HP column of the biologically active agent of the present invention.
Figure 4:
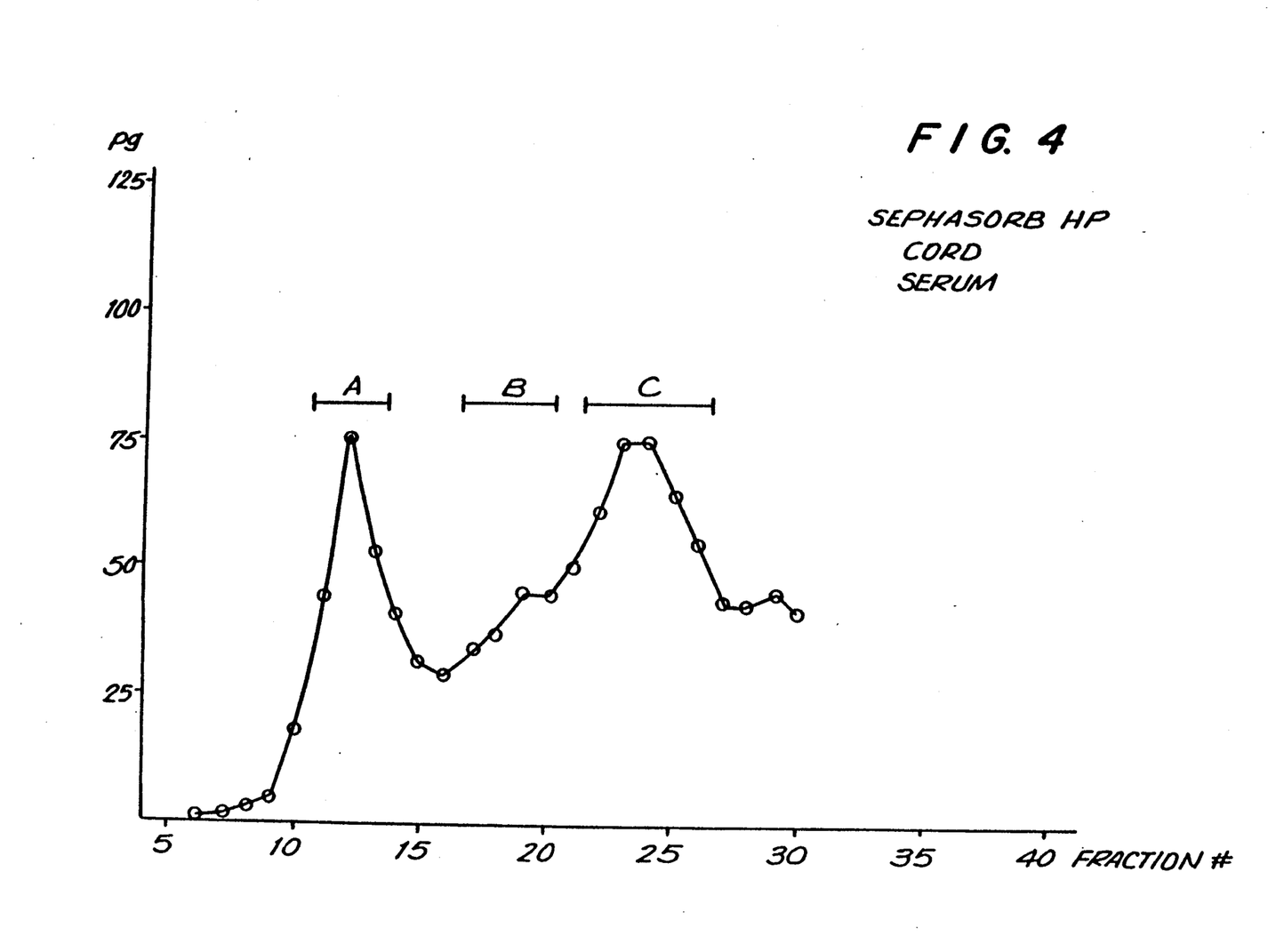
FIG. 4 is a plot of the elution profile from a Sephasorb HP column of a cross-reactive material present in human cord serum.

The final extract from Step 1 was chromatographed on Sephasorb HP (Pharmacia, Piscataway, NJ) with an SR-25 column (2.5 cm wide ×30 cm high). The solvent mixture applied to the column was methanol:water (1:1). The column was eluted in an upward flow mode (200 ml/hr) with a WIZ Model P pump (ISCO, Lincoln, NB). Sixty fractions of 4 ml each were collected. Samples were applied via 1.8 ml sample loop generated by two four-way valves (SRV-4, Pharmacia, Piscataway, NJ). With this method, all materials in contact with the solvent stream were either stainless steel, Teflon or borosilicate glass in order to avoid non-specific binding. The final extract prepared as in Step 1 above was in a total volume of 9 mls and was chromatographed in five portions. Aliquots of the chromatography fractions were assayed for digoxin immunoreactivity with reagents obtained from New England Nuclear (Boston, MA) as described below in Example 2 using the manufacturers instructions except that 0.2 ml instead of 0.5 ml of both antibody and tracer was used. This was done to increase the sensitivity of the assay. The results are shown in FIG. 1. Four peaks of activity were resolved using this column. This should be compared with FIG. 4 demonstrating the behavior of material isolated from human cord serum which cross-reacts with digoxin antibodies but does not possess any hypotensive activities. Very little of the activity isolated from cord serum was found in the region of the chromatogram where the peak of the biologically active agent of the present invention was detected using a Sephasorb HP column under identical conditions.

The fractions corresponding to the immunoreactive peaks (K3A, K3B, K3C and K3D) were pooled, the solvents removed under vacuum and water removed by lyophilization.

Step 3: Chromatography of K3B on Sephadex LH-20 with An Eluant of Acetonitrile : Water (7:3)

Figure 2:
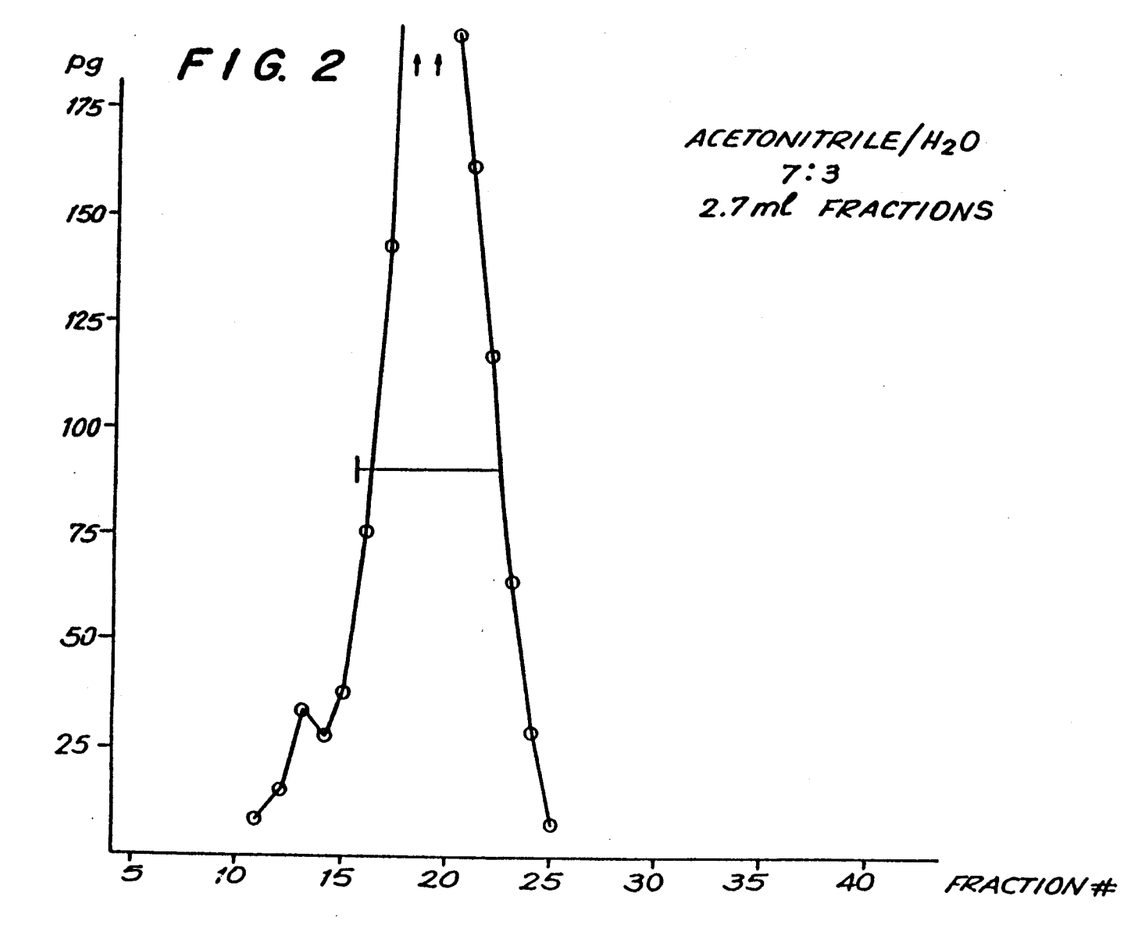
FIG. 2 is a plot of the elution profile from a Sephadex LH-20 column of the biologically active agent of the present invention using an acetonitrile:water eluant (7:3).

The K3B peak (fractions 23-26) obtained from Step 2 was chromatographed on Sephadex LH-20 with a solvent mixture consisting of acetonitrile:water (7:3). The column (1.9 cm wide×30 cm high) was eluted by gravity and 40 fractions of 2.7 ml each were collected. Samples (5 ml) were applied directly to the bed of the column. Additional solvent was then applied until the active fractions were eluted. The amount of biologically active agent was determined in each fraction using the assay described above. The results are shown in FIG. 2. The agent was found in fractions 16-22. Fractions 16-22 were pooled, lyophilized to dryness, and re-chromatographed on Sephasorb HP. The peak activity was found in fractions 22-26, demonstrating the reproducible nature of the behavior of this material (previously on this column, the agent peaked in fractions 23-26).

Step 4: Chromatography on Sephadex LH-20 with an Eluant of Methanol

Figure 3:
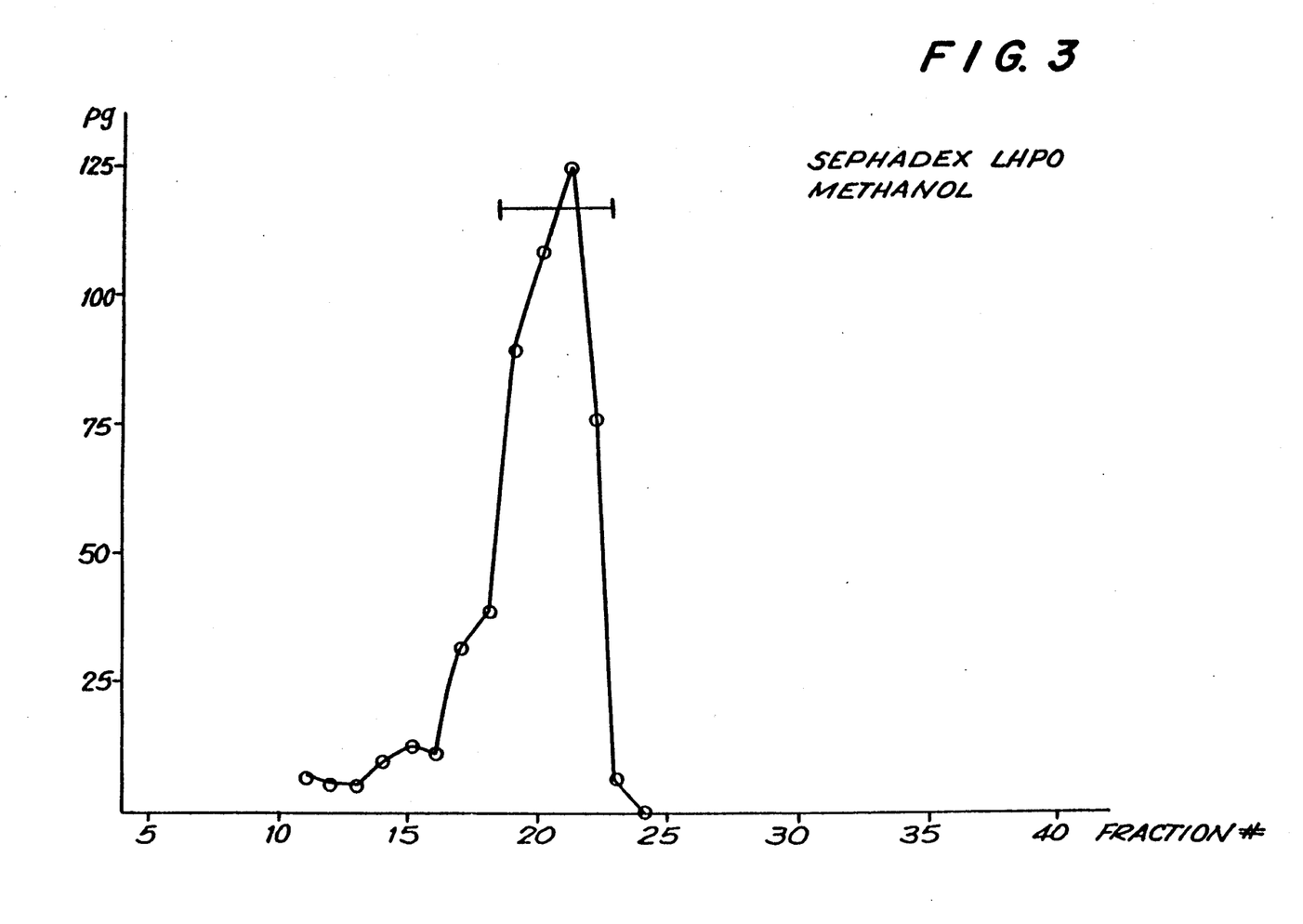
FIG. 3 is a plot of the elution profile of the biologically active agent of the present invention from a second Sephadex LH-20 column using methanol as the eluant.

Fractions 22-26, isolated from the second Sephasorb HP column were chromatographed using the same protocol that was used for Step 3, except that methanol was used for the elution step. The results are shown in FIG. 3, where the agent was eluted in fractions 19-22. Each peak was separately pooled and lyophilized to dryness. Each fraction was redissolved in 2 ml of water and lyophilized to dryness for storage.

EXAMPLE 2

Assay for Determination of Digoxin Immunoreactivity

The presence of the biologically active agent of the present invention is detected by its ability to react with digoxin antibodies. A typical assay is performed as follows. Standard solutions, containing known amounts of digoxin, were prepared by diluting standards provided by the manufacturer (New England Nuclear, Boston, MA, cat. no. A082). Standard curves were prepared by adding 0.1 ml of standard solutions containing 0.05, 0.1, 0.2, 0.5, 1.0 and 2.0 ng/ml of digoxin to 12×75 mm borosilicate culture tubes (Fisher Scientific Co.) and assaying as described below.

Unknown samples were pipetted into 12×75 mm culture tubes and evaporated to dryness under a stream of nitrogen. 0.2 ml of [$^{125}$I]-labeled digoxin-tracer and 0.2 ml of digoxin antibody were added to each tube. The tubes were mixed by vortex and allowed to incubate for 30 minutes at room temperature. Thereafter, the tubes were centrifuged at 2600×g at 4° C. for 30 minutes and transferred to foam decanting racks (Diagnostic Products, Los Angeles, CA) and decanted. Each tube was blotted and the amount of [$^{125}$I] was determined using a gamma counter (Model 1275 Mini-gamma, LKB, Gaithersburg, MD). Individual values of digoxin were determined by interpolation against the standard curve obtained at the same time using a smooth line best fit program from LKB and are expressed as ng digoxin equivalents, as described above.

EXAMPLE 3

Assay for the Endogenous Biologically Active Agent

Sprague-Dawley rats, weighing 270–305 grams, were used in all experiments. Four rats were anesthetized with a single intraperitoneal injection of pentobarbitol, 30–40 mg/kg body weight. Polyethylene catheters were injected into the right carotid artery, left external jugular vein and bladder. Upon completion of the surgical procedure, the animals were given a priming injection of 0.15M NaCl solution equal to 0.5% body weight. In order to monitor renal function, an infusion of 0.15M NaCl solution was started at 0.045 ml/min and contained $^{14}C$-inulin and $^3H$-PAH (para-aminohippuric acid) (New England Nuclear, Boston, MA) in quantities designed to provide 5 micro Ci per hour and 10 micro Ci per hour of the two radioactive isotopes, respectively. After an equilibration period of 40–50 minutes, the experiment was commenced.

The intra-arterial blood pressure was recorded using a transducer and an eight-channel physiography (Beckman, Palo Alto, CA). The pressure tracing was calibrated using a manual sphygmomanometer. The hematocrit values were measured by routine techniques well known in the art. The plasma and urinary activity of $^{14}C$-inulin and $^3H$-PAH were measured using a beta scintillation counter (Rackbeta, LKB Instruments, Gaithersburg, MD). The plasma electrolytes were measured using a flame photometer (Klinaflame, Beckman Instruments, Palo Alto, CA). The glomerular filtration rate (GFR) and renal blood flow were calculated from the $^{14}C$-inulin and $^3H$-PAH clearances, respectively, using standard equations.

In the first study, a 1% aliquot of a 25-fold concentrate (17 ng digoxin equivalents) obtained from a Type 1 highpotassium human female breast cyst fluid (K3, above) was dissolved in 1 ml of 0.15M NaCl, and the entire volume was injected intravenously. In the second and third studies, a 2nd 1% aliquot obtained from a Type 1 high-potassium human female breast cyst fluid (K3) was dissolved in 2 ml of 0.15M NaCl and 1 ml was administered (8.5 ng digoxin equivalents). In the fourth study, the material obtained from Step 4 above (fractions 19–22, K3B) and which represented 100-fold-concentrate of the original breast cyst aspirate was dissolved in 1 ml of 0.15M NaCl and 0.2 ml was injected (representing 13.5 ng digoxin equivalents).

Blood pressure was recorded continuously for the duration of the study. Blood samples, 0.3 ml in volume, were removed every 30 min and replaced with an equal volume of saline. Adequate urinary drainage was successfully maintained only in the first study; technical problems prevented measurements of renal function in the final three experiments.

The experimental results are summarized in Table 1.

TABLE 1

| Study Number | Material Injected | Volume Injected | Initial B.P. | Lowest B.P. | Time (min) to Max Response | Hematocrit Initial | Hematocrit Final |
|---|---|---|---|---|---|---|---|
| 1* | 25-fold concentrate of crude cyst fluid (K3) dissolved in 1.0 ml | 1.0 ml | 105–110 | 60 | 20 | 39 | 20 |
| 2 | 25-fold concentrate of crude cyst fluid (K3) dissolved in 2.0 ml | 1.0 ml | 115 | 90 | 150 | 52 | 36 |
| 3 | 25-fold concentrate of crude cyst fluid (K3) dissolved in 2.0 ml | 1.0 ml | 115–120 | 75–80 | 20 | 50 | 28 |
| 4** | 100-fold concentrate of cyst fluid (K3B) dissolved in 1 ml | 0.2 ml | 105 | 60 | 30 | 48 | 28 |

*GFR rose from 0.18 ml/min during control period to 0.28 ml/min after administration.
**Final plasma values; $Na^+$ 141 mmol/L, $K^+$ 5.4 mmol/L.

In each study in which one animal received the biologically active agent, there was a significant decline of blood pressure that was irreversible in Experiment 1 (resulting in expiration of the test animal) and partially reversible in 2 and 3. In Experiment 3, the decline in blood pressure was maximal within 15 min; this was followed by a gradual return to the baseline blood pressure value over 20–40 min. There was a consistent fall in the hematocrit so that the final determination equalled 51, 69, 57 and 58% of the initial value in the four experimental subjects, respectively. The reason for the fall in the hematocrit is unknown. However, when the cells were counted, there was no decline in the actual number of cells (the hematocrit is based on the volume, not the number of cells).

In animal 1, the only animal for which glomerular filtration (GFR) could be determined, the single kidney value was 0.18 ml/min prior to injection of the biologically active agent of the present invention. It rose to 0.32 and 0.24 ml/min in the two urine collections completed after administration of the biologically active agent. The plasma sodium and potassium concentration measured at the completion of the fourth experiment in which the animals received the most purified material were 141 and 5.4 mmol/L, respectively, which are normal values.

In addition, a highly purified fraction, obtained as the final extract from Step 4 above, was administered to an animal. The protocol followed was identical to the studies presented in Table 1. The data is shown in Table 2 below.

TABLE 2

| Study Number | Material Injected | Volume Injected | Initial B.P. | Lowest B.P. | Time (min) to Max Response | Hematocrit Initial | Hematocrit Final |
|---|---|---|---|---|---|---|---|
| 5 | 70 pg | 0.010 ml | 140 | 120 | 25 min. | N.D.* | N.D. |
| 5' | 160 pg | 0.025 ml | 120 | 60 | 15 min. | N.D. | N.D. |

*Not done

In this study, the most purified fraction, from Step 4 above was used. Administration of this material lead to a rapid fall in blood pressure, as was observed with the less purified samples. Moreover, the same animal was given a second dose of the active biological agent (5', Table 2), representing 160 pg digoxin equivalents. This lead to a further lowering of blood pressure.

The results of this example illustrate that administration to mammals of the biologically active agent of the present invention results in prompt reduction in blood pressure levels. It is clear from these experiments that the biologically active agent of the present invention functions well as an anti-hypertensive agent (i.e. a hypotensive agent).

EXAMPLE 4

Behavior of Breast Cyst Fluid Derived Agent After Treatment with Glusalase

A portion of sample K3B (from Example 1) was treated with Glusalase, an extract from the snail Helix Pomatia (Endo Laboratories, Garden City, NY) that contains a mixture of sulfatases and glucuronidases. Whereas, prior to treatment, the samples could not be extracted from water with ethyl acetate, after enzyme digestion, ethyl acetate extracted the agent from water. Thus, the samples have the properties of steriod conjugates, containing sulfates and/or glucuronic acid.

Figure 5:
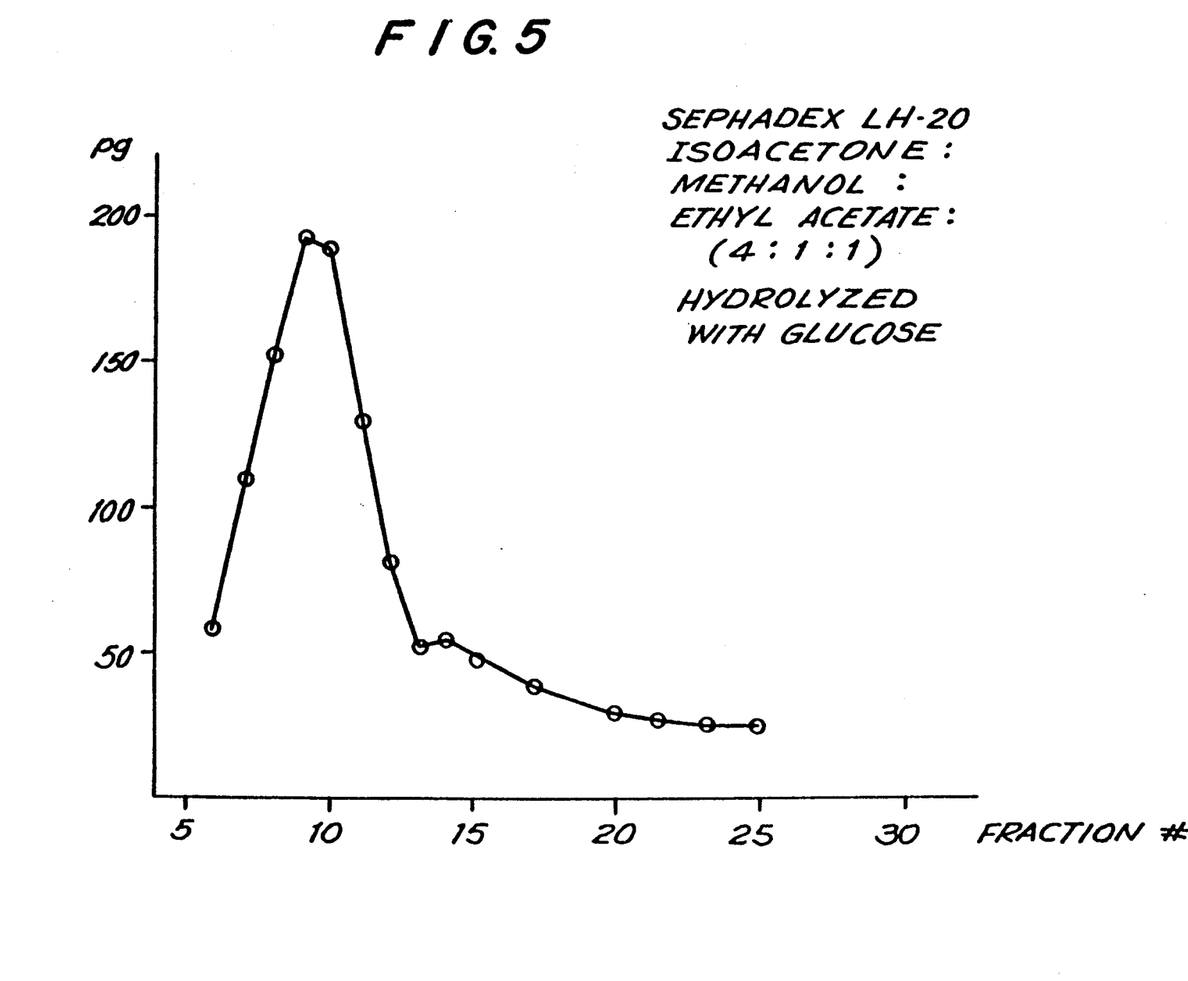
FIG. 5 is the elution profile from a Sephadex LH-20 column of the biologically active agent of the present invention after digestion with Glusalase, using iso-octane:methanol: ethyl acetate (4:1:1) as the eluant.

The Glusalase-digested samples were re-chromatographed on Sephasorb HP as above except samples were eluted using isooctane:methanol:ethyl acetate (4:1:1) as the eluant, and aliquots of each fraction assayed by digoxin radioimmunoassay as described above. The data is presented in FIG. 5. The agent eluted earlier after digestion with glusalase than undigested material (compare with FIG. 1). This is consistent with the above extraction data, demonstrating that the biologically active agent of the present invention is a steriod conjugate.

Hydrolysis did not alter the amount of the biologically active agent (as detected by digoxin immunoassay) present in these fractions. This implies that neither the nature of the conjugate nor its presence or absence affects this assay.

The invention has been described above with reference to preferred embodiments. It would be obvious to one, of ordinary skill in the art that many additions, deletions and/or modifications could be made without departing from the scope of the invention as claimed below.

EXAMPLE 5

Streamlined Extraction and Purification Procedure 100 ml of pooled Type 1 fluid were mixed with an equal volume of acetonitrile, and insoluble material was removed by centrifugation. The extract (supernatant) was mixed with an equal volume of ethyl acetate, and separated into two phases in a separatory funnel. The lower, aqueous phase was discarded. The volatile solvents were removed from the upper phase with a conventional rotary evaporator (Buchler, Fort Lee, NJ) under a vacuum at room temperature, and the remaining liquid was eliminated by lyophilization.

Figure 6:
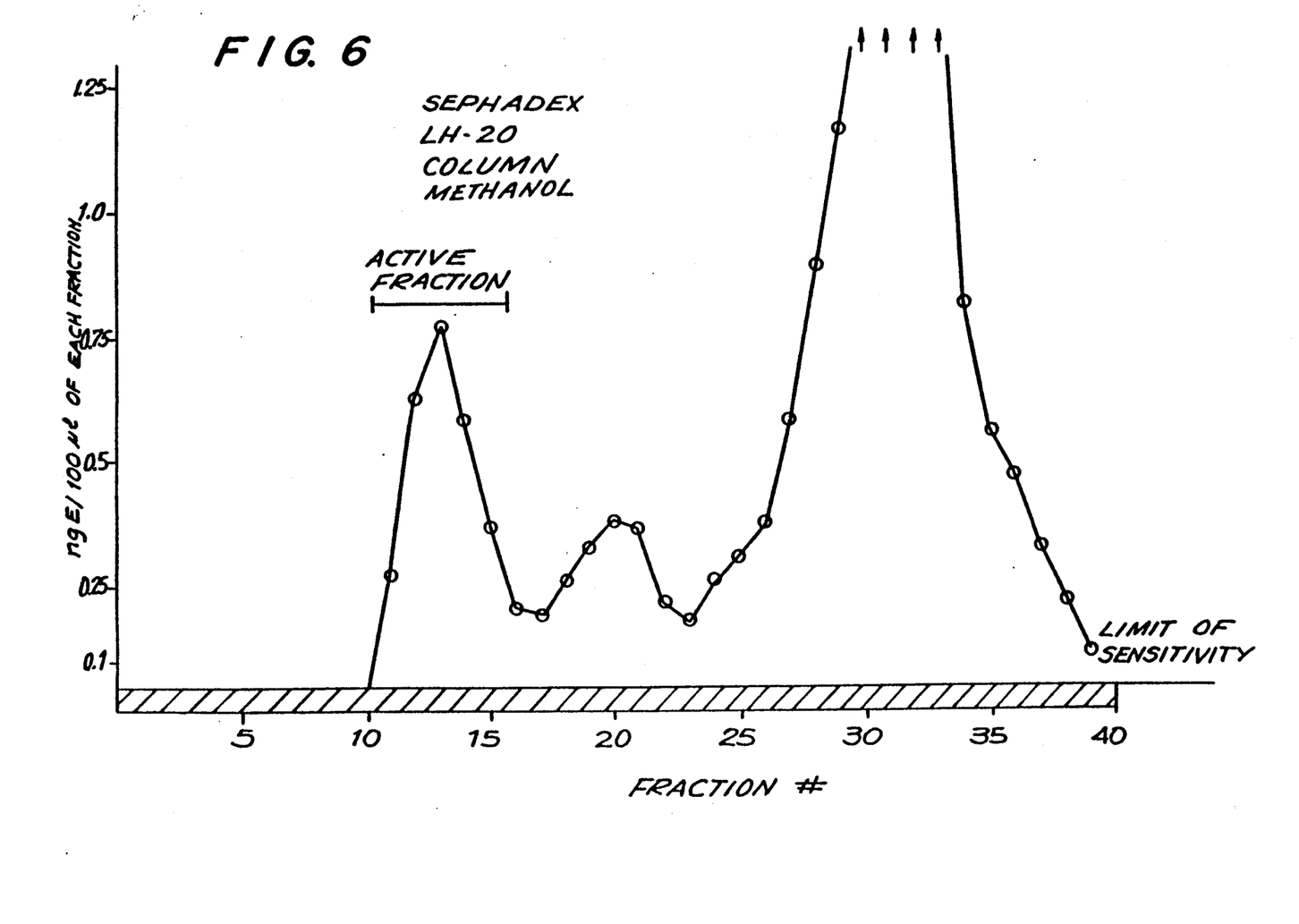
FIG. 6 is a plot of the elution profile from a Sephadex LH-20 column of the biologically active agent of the present invention extracted using methanol as the eluant.

The lyophilizate was extracted with methanol (5-10 ml) and applied to a Sephadex LH-20 (Pharmacia, Piscataway, NJ) column (1.9×30 cm) prepared in the same solvent. Fractions of 5 ml were collected and aliquots were evaporated to dryness and assayed for digoxin equivalents as described above. This is shown in FIG. 6. Fractions 11-14 containing the biologically active agent were pooled and evaporated to dryness under nitrogen gas at room temperature.

Figure 7:
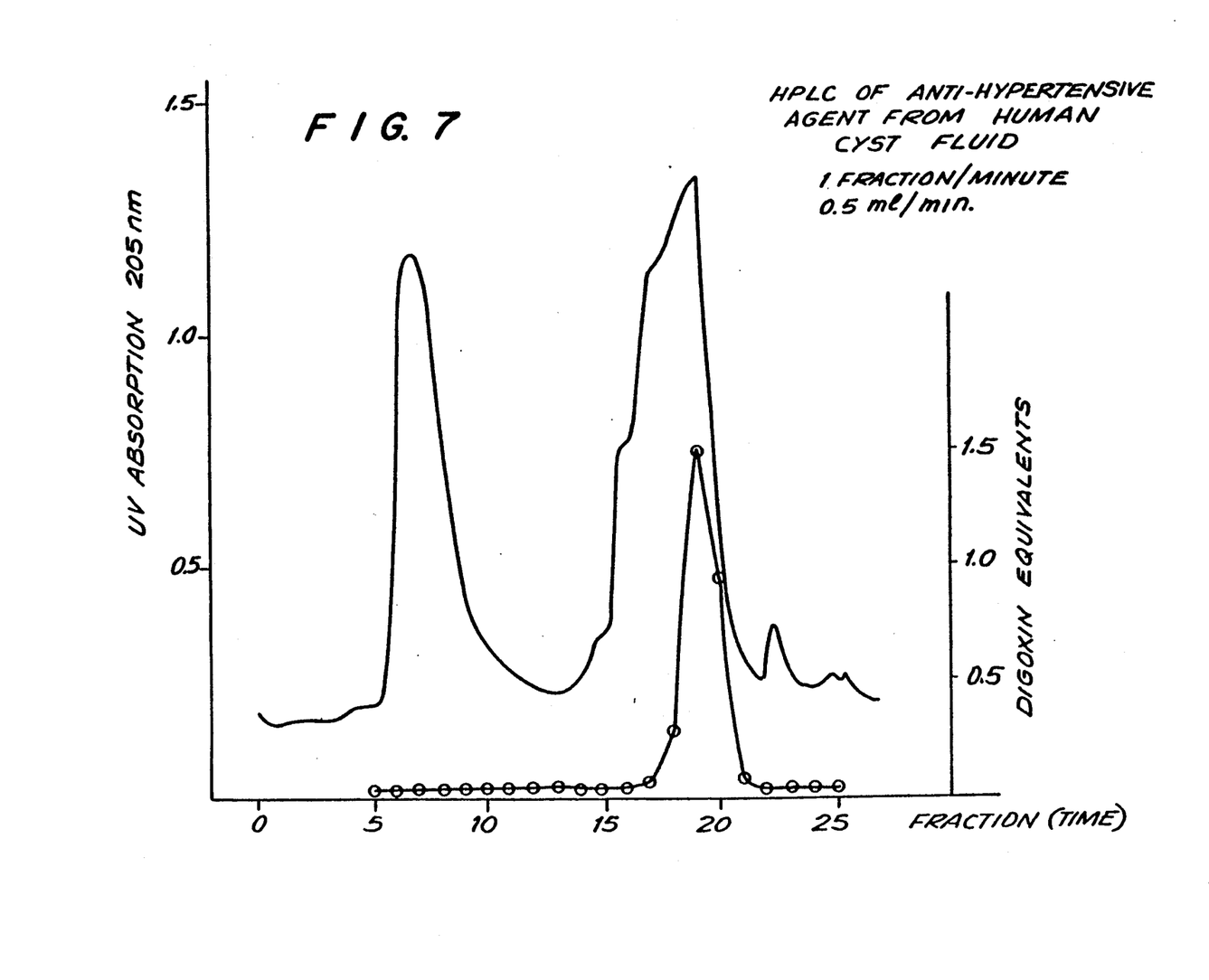
FIG. 7 is a plot of the elution profile of the biologically active agent of the present invention from an amino carbohydrate high-pressure liquid chromatography (HPLC) column eluted with a gradient of acetonitrile : water.
Figure 8:
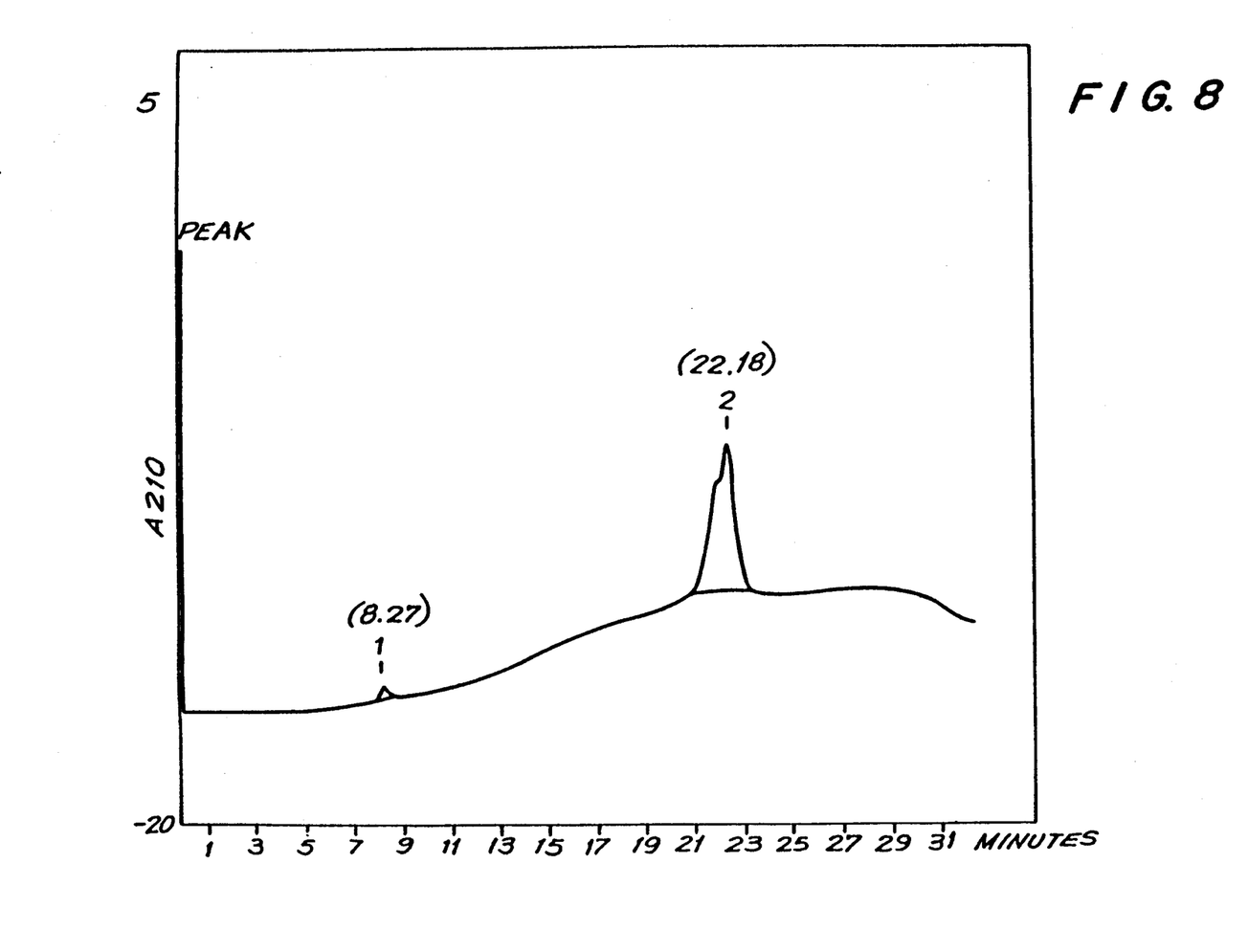
FIG. 8 is a plot of the elution profile of the biologically active agent of the present invention from a second amino carbohydrate HPLC column eluted with a gradient of acetonitrile : water, demonstrating its absorbance at 210 nM.

The biologically active agent was further purified by HPLC column (LKB, Gaithersburg, MD) using an amino carbohydrate column (Alltech, Chicago, IL). The column was eluted with a 20-minute gradient starting at 95% acetonitrile : 5% water to 55% acetonitrile : 45% water. Alternatively, an isocratic (i.e. a constant concentration or non-gradient) elution scheme employing the same acetonitrile : water concentration ratios, or a mixture of methanol and water (either in a gradient or isocratically) could have been used. Column fractions (0.5 ml each, 1 fraction per minute) were collected, as shown in FIG. 7, and fractions 19 and 20 were found to contain the biologically active agent. These fractions were reinjected again into a HPLC column employing the same absorbent (amino carbohydrate). A representative chromatogram of the biologically active agent recovered from the second amino carbohydrate column is shown in FIG. 8. Fraction 22 contained the purified biologically active agent.

EXAMPLE 6

Stimulation of Ouabain Binding to the Ouabain receptor by the Biologically Active Agent The present inventors have also unexpectedly discovered that the purified biologically-active agent of the present invention has the ability to stimulate the binding of ouabain to the ouabain receptor located on the cell surface. This was a most surprising finding in that the biologically active agent of the present invention stimulated the cellular Na+, K+ At Pase enzyme, whereas ouabain is known to inhibit this enzyme.

This was demonstrated as follows. Beef kidney was homogenized in 0.25M sucrose (3:1 volume:weight) in a Waring blender and subjected to differential centrifugation using a GSA rotor (Dupont Sorval, Wilmington, DE) at 7000×g and 38,000×g using a SA-600 rotor (Dupont Sorval, Wilmington, Delaware) for 30 minutes each. The resulting crude microsomal preparation was resuspended in Buffer 1 (Buffer 1=100 mM NaCl, 50mM Tris/HCl, 0.25mM Na$_2$EDTA, 5mM MgCl$_2$, pH=7.4), to which had been added 20% glycerol (at a ratio of 1 ml to 3 grams fresh weight of beef kidney) and used as the source of ouabain receptor. Ouabain binding to its receptor was measured by incubating [$^3$H]-ouabain (New England Nuclear, Boston, MA) in buffer 1 to which had been added 0.5 mM ATP. Aliquots of the biologically active agent which had been evaporated to dryness at room temperature under a stream of nitrogen gas and redissolved in Buffer 1 were then added. The amount of the biologically active agent used was between about 1 and 50 picogram digoxin equivalents per tube. Fifty microliters of the beef kidney microsomal preparation were added, and the mixture was incubated for two hours at 37° C. prior to the addition of the labeled ouabain (5 nCi [$^3$H]-ouabain) and for 20 minutes at 37° C. after the addition of the labeled ouabain tracer. At the conclusion of the incubation, the mixture was chilled for ten minutes in an ice bath. Bound ouabain was separated from unbound ouabain by filtration through glass fiber filters (GFC Filters, Whatman, Springfield, NJ).

Under the conditions described above, the biologically active agent caused an increase in ouabain binding from an initial 9% to about 20% of the total added, which represents a 2.2 fold increase. The data are shown in Table 3 below.

TABLE 3

| Addition | CPM* Bound | % |
|---|---|---|
| Binding Protein | 761 | 9.3 |
| Binding Protein + 10 ul (1.2 pg) | 1039 | 12.8 |
| Binding Protein + 15 ul (1.8 pg) | 1234 | 15.2 |
| Binding Protein + 25 ul (3.0 pg) | 1437 | 17.7 |
| Binding Protein + 50 ul (6.0 pg) | 1688 | 20.8 |

*Input [$^3$H]-ouabain = 8099 CFM

The increased amount of labeled ouabain bound could be displaced by unlabeled ouabain without any change in the kinetic constants indicating that the strength of the binding of ouabain to its receptor was not affected by the agent of the present invention. This increase in ouabain binding to the ouabain binding proteins was not observed with extracts from breast cyst fluid with high sodium levels (Type 2 breast cyst fluids). The present inventors do not know of any other substance which displays this property.

What is claimed is:

1. A method for purifying a biologically active agent comprising a factor isolated from Type 1 human female breast cyst fluid, said factor being immunoreactive with digoxin antibodies and having anti-hypertensive activity in mammals, said method comprising the steps of:

agitating Type 1 human female breast cyst fluid with a lower alcohol, thereby causing precipitation of undesirable constituents in said fluid, discarding the precipitate, mixing the alcohol-solubilized factor with first polar solvent to form a second precipitate, discarding the second precipitate, evaporating said first polar solvent and recovering a first aqueous phase containing said factor, further extracting said first aqueous phase with a second polar solvent, said second polar solvent being less polar than said first polar solvent obtaining an organic phase containing said agent, removing said second polar solvent from said organic phase and obtaining a second aqueous phase containing said agent, lyophilizing said second aqueous phase, extracting said lyophilizate with methanol-weater, subjecting said extract to chromatography on pressure stabilized polydextran, and recovering fractions containing said agent.

2. The method of claim 1 wherein said agent is purified by chromatography on Sephadex LH-20.

3. A method for purifying a biologically active agent comprising a factor isolated from Type 1 human female breast cyst fluid, said factor being immunoreactive with digoxin antibodies and having anti-hypertensive activity in mammals, said method comprising the steps of:

agitating Type 1 human female breast cyst fluid with a first polar solvent, thereby causing a precipitation of undersirable constituents in said fluid, discarding the precipitate, mixing the solubilized factor with a second polar solvent, and recovering an organic phase containing said factor, said second polar solvent being less polar than said first polar solvent, removing said second polar solvent from said organic phase and obtaining an aqueous phase containing said agent, lyophilizing said aqueous phase, extracting said lyophilizate with a methanol-water mixture, subjecting said extracted lyophilizate to hydrophobic affinity chromatography, and recovering fractions containing said agent.

4. The method of claim 2 wherein said agent is further purified by chromatography on an amino carbohydrate column.

5. The method of claim 2 wherein said agent also has the property of stimulating the binding of ouabain to the cellular ouabain receptor.

6. The method of claim 2 wherein said agent is further characterized by absorbing light at 210 nm of the spectrum.

* * * * *